(12) United States Patent
Pape et al.

(10) Patent No.: US 10,190,974 B2
(45) Date of Patent: Jan. 29, 2019

(54) OPTICAL GAS SENSOR COMPRISING AN LED EMITTER FOR THE EMISSION OF LIGHT OF A NARROW BANDWIDTH

(71) Applicant: Dräger Safety AG & Co. KGaA, Lübeck (DE)

(72) Inventors: Andre Pape, Lübeck (DE); Arne Tröllsch, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 15/525,338

(22) PCT Filed: Nov. 2, 2015

(86) PCT No.: PCT/EP2015/002195
§ 371 (c)(1),
(2) Date: May 9, 2017

(87) PCT Pub. No.: WO2016/074773
PCT Pub. Date: May 19, 2016

(65) Prior Publication Data
US 2017/0322149 A1    Nov. 9, 2017

(30) Foreign Application Priority Data
Nov. 10, 2014    (DE) .................. 10 2014 016 515

(51) Int. Cl.
*G01N 21/3504*    (2014.01)
*G01J 3/42*    (2006.01)
(Continued)

(52) U.S. Cl.
CPC ........... *G01N 21/3504* (2013.01); *G01J 3/42* (2013.01); *G01N 21/1702* (2013.01); *G01N 21/31* (2013.01)

(58) Field of Classification Search
CPC .............. G01N 21/3504; G01N 21/31; G01N 21/1702; G01J 3/42
See application file for complete search history.

(56) References Cited

U.S. PATENT DOCUMENTS 4,560,875 A    12/1985    Crowder
4,567,366 A *    1/1986    Shinohara ............ G01N 21/255
                                                                 250/339.13
(Continued)

FOREIGN PATENT DOCUMENTS

DE    40 11 462 C2    1/1995
DE    100 47 728 A1    4/2002
(Continued)

OTHER PUBLICATIONS

Harvey Hardaway et al: "Optimizing indium aluminum antimonide LEDs and photodiodes for gas sensing applications", Medical Imaging 2002: Pacs and Integrated Medical Information Systems: Design and Evaluation, vol. 5564, Oct. 22, 2004 (Oct. 22, 2004), pp. 105-112.
(Continued)

*Primary Examiner* — Sang H Nguyen
(74) *Attorney, Agent, or Firm* — McGlew and Tuttle, P.C.

(57) ABSTRACT

An optical gas sensor (1), for quantitatively measuring a concentration of one or more gases, includes a radiation source (2) for emitting light waves (L), a cuvette (3) for holding a gas (G) to be measured, and a detector (4) for measuring light intensities. The light source (2) includes at least one emitter (5) of light waves (L) and is configured to emit light waves (L) of at least one first wavelength and of a second wavelength different from the first wavelength simultaneously or separately from each other. The emitter (5) is further configured to emit a spectrum the full half-life width of which is a maximum 50% of the effective wavelength, and to emit light waves (L) having a controlled beam
(Continued)

path. The detector (4) is configured to quantitatively detect an intensity of emitted light waves (L) of the first wavelength and of the second wavelength.

10 Claims, 2 Drawing Sheets

(51) Int. Cl.
*G01N 21/31* (2006.01)
*G01N 21/17* (2006.01)

(56) References Cited

U.S. PATENT DOCUMENTS

| | | | |
|---|---|---|---|
| 5,166,514 A | 11/1992 | Schmid | |
| 5,448,071 A * | 9/1995 | McCaul | G01N 21/274 250/343 |
| 6,455,854 B1 * | 9/2002 | Richman | G01N 21/314 250/339.01 |
| 6,791,689 B1 | 9/2004 | Weckstroem | |
| 7,999,232 B2 | 8/2011 | Wilson et al. | |
| 9,008,742 B2 * | 4/2015 | Naganuma | A61B 5/0095 600/310 |
| 2002/0036266 A1 * | 3/2002 | Dreyer | G01N 21/3504 250/345 |
| 2009/0235720 A1 * | 9/2009 | Smith | G01J 3/02 73/31.05 |
| 2012/0075632 A1 * | 3/2012 | Baasner | G01N 21/3504 356/437 |
| 2013/0306838 A1 * | 11/2013 | Matsushita | G02B 26/001 250/206 |
| 2015/0099274 A1 * | 4/2015 | Axelrod | C12M 41/34 435/39 |
| 2015/0300948 A1 * | 10/2015 | Buchtal | G01N 21/3504 356/454 |

FOREIGN PATENT DOCUMENTS

| | | |
|---|---|---|
| DE | 202 02694 U1 | 7/2002 |
| GB | 2 240 639 A | 8/1991 |
| GB | 2 391 310 A | 2/2004 |
| WO | 2007/091043 A1 | 8/2007 |
| WO | 2012/001633 A2 | 1/2012 |

OTHER PUBLICATIONS

Desmond Gibson et al: "A Novel Solid State Non-Dispersive Infrared C02 Gas Sensor Compatible with Wireless and Portable Deployment", Sensors, vol. 13, No. 6, May 29, 2013 (May 29, 2013), pp. 7079-7103.

* cited by examiner

OPTICAL GAS SENSOR COMPRISING AN LED EMITTER FOR THE EMISSION OF LIGHT OF A NARROW BANDWIDTH

CROSS REFERENCE TO RELATED APPLICATIONS

This application is a United States National Phase Application of International Application PCT/EP2015/002195, filed Nov. 2, 2015, and claims the benefit of priority under 35 U.S.C. § 119 of German Application 10 2014 016 515.9, filed Nov. 10, 2014, the entire contents of which are incorporated herein by reference.

FIELD OF THE INVENTION

The present invention pertains to an optical gas sensor for quantitatively measuring the concentration of one or more gases.

Optical gas sensors make possible both a qualitative determination of the presence of one or more gases and a quantitative determination of the concentration of one or more gases. Such gas sensors are used, e.g., in gas detection devices in plants for extracting and processing combustible and/or toxic gases to detect undesired gases being released.

BACKGROUND OF THE INVENTION

Gas sensors, which comprise an emitter, a cuvette (test cell) as well as a detector, are known. In optical gas sensors, the emitter is a light source, e.g., a light bulb, which emits a broad spectrum of light waves, i.e., light waves having a plurality of different wavelengths. The cuvette is preferably an essentially closed space, in which the gas to be measured is located. The cuvette may comprise openings to the outside, which make possible an exchange of gas of the cuvette with an area surrounding the gas sensor. The detector is a light sensor, with which preferably an intensity of light, which reaches the detector, can be measured. In order to detect defined wavelengths of the light, bandpass filters are arranged upstream of the corresponding detectors. Such bandpass filters may be configured to let through one or more wavelengths.

The gas or gas mixture to be measured is introduced into the cuvette during the operation. For this, the cuvette may comprise one or more openings. Light waves emitted by the light source are more or less strongly absorbed by the respective gas depending on the concentration of the ingredients of the gas mixture, as well as on the absorption wavelengths. It is possible in this way to determine which wavelengths were absorbed and how strongly by the gas. Because of known specific absorption properties of different gases, a composition of the gas mixture can be determined from this result.

An optical gas sensor comprising a hollow cylindrical cuvette for holding the gas to be measured is known from DE 202 02 694 A1. A plane mirror on one side and a concave mirror on the other side are arranged at the cuvette in the longitudinal axial direction. The concave mirror comprises a plurality of recesses for accommodating a light bulb and a light wave detector. Light waves emitted by the light bulb are first repeatedly reflected between the plane mirror and the concave mirror until they reach the light wave detector. As a result of this, an optical path length, on which these light waves can be absorbed by the gas or gas mixture to be measured, is extended. Weakly absorbing gases can thus be measured better.

Such a gas sensor has especially the drawback that an arrangement of the light bulb and light wave detectors at the concave mirror can only be produced with great effort because of the curved surface of the concave mirror. Furthermore, a plurality of the light sources used in optical gas sensors have the drawback of emitting a relatively broad spectrum of light waves. Thus, not only are light waves emitted with wavelengths that are needed for measuring the gas concentration, but also light waves with wavelengths which are not of significance for measuring the gas concentration and have to be filtered out by a bandpass filter to avoid measuring errors. As a result, the efficiency of the optical gas sensor is adversely affected. In particular, light bulbs have, moreover, the drawback that a large percentage of electrical energy is converted into heat, which has to be dissipated as heat due to energy losses. This leads to an excessive energy consumption of the gas sensor and is especially disadvantageous for mobile applications, which are supplied with power via an internal power source, e.g., a battery. The life of the battery and thus the operating time of the mobile gas sensor are markedly reduced due to the increased power consumption.

SUMMARY OF THE INVENTION

On the basis of this state of the art, a basic object of the present invention is to provide an optical gas sensor, which does not have at least some of these drawbacks. Hence, an object of the present invention is to provide an optical gas sensor, with which especially concentrations of weakly light-wave-absorbing gases can be quantitatively measured and which has an improved efficiency.

According to the invention an optical gas sensor is provided for quantitatively measuring the concentration of one or more gases. The optical gas sensor comprises a radiation source for emitting light waves, a cuvette (test cell) for holding a gas to be measured and a detector for measuring light intensities. The radiation source comprises at least one emitter of light waves, e.g., an LED and is configured to emit light waves of at least one first wavelength and of a second wavelength different from the first wavelength simultaneously as well as separately from one another. The emitter is preferably configured to emit a spectrum, the full width at half maximum of which is a maximum 50% of the effective wavelength. The emitter is preferably further configured to emit a discrete spectrum, the full width at half maximum of which is a maximum 20% of the effective wavelength. The detector is configured to quantitatively detect an intensity of the emitted light waves of the first wavelength and of the second wavelength. The emitter is preferably configured to convert at least 80% of the electrical energy consumed by the emitter into light waves.

The underlying idea of the present invention is that the efficiency of the optical gas sensor can be considerably improved by using such an emitter. As a result, less heat is produced and thus less electrical energy is consumed during the generation of light waves. Less heat is generated during the conversion of electrical energy into light waves by means of an LED than, e.g., by a light bulb, as they are used in many conventional gas sensors. Thus, the gas sensor has a lower power consumption during the operation. This is especially advantageous for mobile applications because the loading cycle of a storage battery or the life of a battery of the mobile application can be markedly extended as a result.

Due to the separate emitting of light waves of different wavelengths, e.g., a main signal as well as a reference signal can be generated, and the reference signal can be used for checking the measurement results of the main signal. For example, an embodiment for the quantitative determination of methane should be mentioned here. In this connection, the measuring wavelength of the measured signal is selected to be approximately 3.2 µm, and suitable reference wavelengths for the reference signal appear at 3.1 µm and/or at 3.9 µm.

The more light waves of different wavelengths can preferably be generated separately, the more gases can be quantitatively determined with the gas sensor according to the present invention. The result is that the emitter emits only a light spectrum of a relatively narrow bandwidth. The light waves are preferably in the infrared range because of the absorption properties of gases.

Emitters which are configured as LEDs have the advantage that relatively short light pulses can be emitted with them without the LEDs emitting an afterglow after the light pulse like a light bulb does. The individual LEDs can thus emit light pulses essentially one directly after another, so that, e.g., the measured signal and the reference signal extend due to an essentially constant gas mixture arranged in the cuvette. As a result, measurement errors are avoided or reduced. Furthermore, LEDs have the advantage that they are suitable for emitting a light spectrum of a relatively narrow bandwidth and have an especially good efficiency in the conversion of electrical energy into light waves. The special optical properties of LEDs in the configuration as emitters are, for example, known from the area of optical signal transmission with fiber-optic waveguides. In particular, the narrow bandwidth of the emitted spectrum, due to the full width at half maximum and the effective wavelength, are explained, for example, in DE 40 11 462 C2.

The detector is, e.g., a photodiode, which generates a current during the reaching of light waves, the amperage of which depends on the intensity of the light waves. Thus, the degree of absorption of the light waves of a defined wavelength can be determined by the gas as well as by the species of the gas or composition of the gas mixture. At least one detector is preferably configured to detect a plurality of different, preferably disjunctive wavelength ranges. Thus, at least two different gases can be detected with a cuvette and a detector in a simple and cost-effective manner.

A corresponding bandpass filter can be arranged in front of the detector, e.g., to avoid interfering effects. Depending on the configuration of the gas sensor, the bandpass filter may be configured as a function of the radiation source. In case of a radiation source, with which, e.g., light waves in four different wavelengths can be emitted, a bandpass filter that is permeable to these four wavelengths is accordingly arranged in front of the detector. Bandpass filters have the additional advantage that light waves, which are not let through by the bandpass filter, can be reflected by same. It may thus be advantageous to arrange a bandpass filter at an emitter or radiation source, so that in case of a plurality of radiation sources with bandpass filters arranged in front of them, less reflection surface of a mirror is lost than without bandpass filters.

The cuvette is preferably configured such that no interfering effects, e.g., light waves coming from a surrounding area of the gas sensor can penetrate into the cuvette or reach the detector. A necessary accuracy of the measurement results of the gas sensor is guaranteed as a result. Further, an air exchange of the cuvette with the surrounding area of the gas sensor can preferably be regulated or is relatively minimal, so that the gas mixture within the cuvette remains essentially constant during a measurement cycle, which comprises at least the one-time emitting of a measured signal as well as of a reference signal. Measurement errors are likewise avoided or reduced as a result.

Furthermore, provisions may be made for the radiation source to comprise at least one first emitter and one second emitter, the first emitter being configured to emit light waves of the first wavelength and the second emitter being configured to emit light waves of the second wavelength. The detector and/or at least one emitter comprise at least one optical filter, e.g., a bandpass filter. The emitters are preferably configured as LEDs. Such a radiation source can be produced easily and requires a relatively small installation space. Provisions may especially preferably be made for the radiation source to be configured to emit a discrete spectrum of light waves. The radiation source is thus configured to generate only light waves of a concrete wavelength or of a relatively narrow range of wavelengths. Provisions may, moreover, be made for a bandpass filter, which further reduces the wavelength range generated by the radiation source, to be arranged in front of the radiation source. A plurality of light waves with wavelengths that are spaced apart from one another within the IR spectrum can especially preferably be generated by the radiation source.

Provisions may preferably be made for the cuvette to comprise a mirror arrangement with a plane mirror and with a concave mirror arranged opposite the plane mirror, wherein an optical axis of the concave mirror is arranged essentially at right angles to the plane mirror. The distance between the concave mirror and the plane mirror preferably corresponds to an integral fraction of the radius of curvature of the concave mirror. A light beam passes through the cuvette between the mirrors many times, e.g., four times or six times, before it reaches the light sensor. This arrangement has the advantage that even weakly absorbing gases to be measured can be measured with a gas sensor of a relatively compact size. A radius of curvature of the concave mirror is preferably variable or the concave mirror can be replaced by concave mirrors with different radii of curvature. As a result, the beam path of the light waves within the gas sensor can be configured as being variable, so that the light waves are often reflected differently between the concave mirror and the plane mirror until they reach the detector depending on the setting of the radius of curvature of the concave mirror. This has the advantage that the gas sensor can be used both for gases to be measured with weak as well as strong light wave absorption.

As an alternative, the mirror arrangement may comprise two plane mirrors arranged essentially facing one another, wherein, e.g., a corresponding reflection of the light beam can be obtained via an adjustment of the radiation source or at least of one mirror. This variant can be produced in an especially simple as well as cost-effective manner.

It is preferred that the angles of incidence to the surface normal of a mirror be as small as possible, i.e., the light waves reach the mirrors almost at right angles. As a result, the effect of interfering factors, e.g., moisture on the mirror surfaces, which causes an absorbing of light waves, is reduced. Furthermore, provisions may be made for the radiation source and/or the detector to be arranged at the plane mirror. The radiation source and the detector can be easily isolated from the interior of the cuvette in such an arrangement, e.g., by a translucent pane or a bandpass filter, so that they have no direct contact with the gas to be measured. This is especially advantageous when fluids arranged in the cuvette may potentially damage the radiation source or detector. Moreover, an arrangement of the radiation source and detector in one plane has the advantage that they can be arranged on a common printed circuit board. Such an arrangement can thus be produced in an especially simple and cost-effective manner. Further, the distance of the radiation source to a point of intersection of the optical axis with the plane mirror preferably corresponds to the distance of a detector to this point of intersection. Such a plane mirror can be mounted especially easily because of its symmetry.

In an especially preferred embodiment of the gas sensor of the present invention, provisions may be made for a radiation source and a detector to be arranged at the cuvette such that light waves which are emitted by the radiation source reach the detector directly. In an advantageous arrangement for this, the radiation source and the detector are not arranged at the same mirror, so that the light waves reach the detector without being reflected. This has the advantage that especially strongly absorbing gases can be determined. Preferably, such a gas sensor comprises at least two radiation sources spaced apart from one another, wherein at least one radiation source is arranged at the cuvette such that light waves emitted by the radiation source reach the detector only via the mirror arrangement.

The gas sensor is preferably configured such that the radiation source is arranged at the cuvette spaced apart from the detector.

The emitter is configured to emit light waves with a controlled beam path. In this connection, the plane mirror and the concave mirror are considered to be components of the cuvette in the sense of the present invention. Such an arrangement is especially advantageously suitable for gas sensors, which are intended for measuring gases that absorb light waves only weakly. The light waves are emitted as a controlled beam path which essentially has no diffuse radiation. This has the advantage that the emitted light is especially efficiently used for detecting gases. Moreover, this is especially advantageous for gas sensors, which are suitable for the detection of gases which have a weak light absorption, because an especially compact construction of the gas sensor is hereby made possible.

It is advantageous when precisely one detector is arranged at the cuvette. In this case, the detector is configured to quantitatively detect light waves essentially only emitted by the radiation source. For this purpose, the detector may comprise, e.g., a corresponding bandpass filter. Such a sensor is especially suitable for applications that require a high precision. As an alternative, the detector may be configured to quantitatively detect a broad spectrum of light waves of different wavelengths, the light waves emitted by the radiation source being part of this spectrum. Such a sensor can be produced in an especially cost-effective manner. The use of only one detector has the advantage that costs for additional detectors can be saved. Furthermore, in case of only one detector and identical size, the cuvette comprises a greater reflection surface of the mirrors, because only one point of a mirror has a detector. Especially the accuracy in the measurement of gases which absorb light waves only weakly can be improved as a result.

In another embodiment of the present invention, at least two radiation sources are arranged at the cuvette spaced apart from one another. This has, e.g., the advantage that the individual radiation sources may have a less complicated configuration. Furthermore, defective radiation sources can be replaced separately from one another. Repair costs or replacement costs can be reduced as a result. In a preferred variant of the present invention, four radiation sources are arranged at the cuvette.

It is especially preferred that the cuvette comprise two detectors, the detectors being configured for measuring light intensities of different radiation sources or different emitters, e.g., different LEDs, of the two radiation sources. In this case, the detectors are preferably arranged such that only light waves of one radiation source can be detected by each detector. As an alternative or in addition, the radiation sources may be connected or modulated differently. This arrangement has the advantage that a plurality of gases to be measured, which are contained in the cuvette, can be quantitatively determined simultaneously.

The gas sensor especially preferably comprises at least one dual bandpass filter, which is preferably arranged at one radiation source. Further, the gas sensor preferably comprises at least one triple bandpass filter, which is preferably arranged at one radiation source. A spectrum of light waves which are emitted by the respective radiation source can consequently be divided into wavelengths or wavelength spectra that are markedly separate from one another.

Further features improving the present invention appear from the following description of a number of exemplary embodiments of the present invention, which are shown in the figures. All features and/or advantages, including structural details and spatial arrangements appearing from the claims, the description or the drawings may be essential to the present invention both by themselves and in the various combinations. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
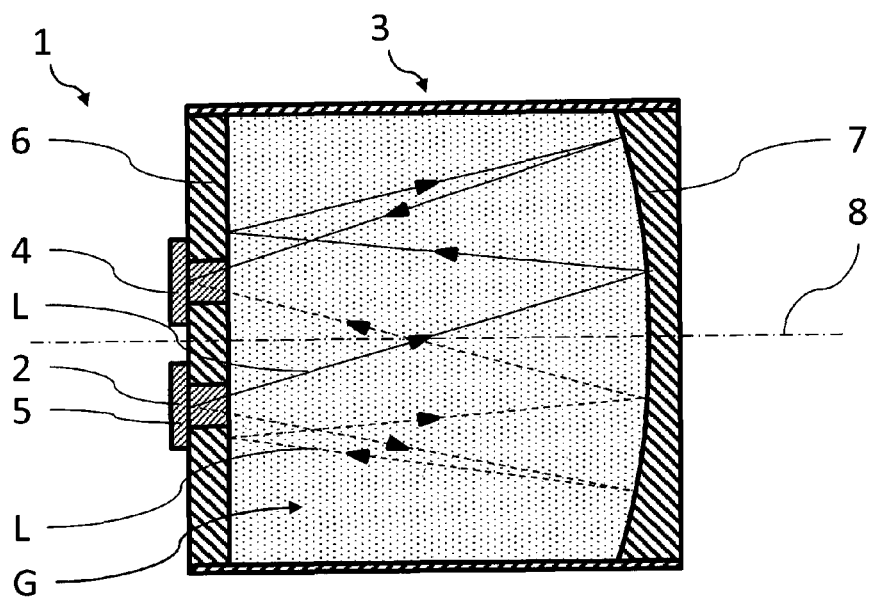
FIG. 1 is a schematic lateral sectional view of a first embodiment of a gas sensor according to the present invention.

Referring to the drawings, the first embodiment of the optical gas sensor 1 according to the present invention shown in FIG. 1 comprises a cuvette 3 having an essentially cylindrical configuration, in which a gas G or a gas mixture to be measured is contained. The cuvette 3 comprises at least one opening, which cannot be seen in this view, for replacing the gas G contained in the cuvette with gas G from the surrounding area of the gas sensor 1. A plane mirror 6 is arranged at one end face of the cuvette 3 and a concave mirror 7 is arranged at another end face. The plane mirror comprises a radiation source 2, which is configured for emitting light waves L of two different wavelengths within the IR spectrum and is oriented in the direction of the concave mirror 7. The radiation source 2 comprises an emitter 5 that is configured as an LED and is configured such that light waves L of different wavelengths can be emitted separately from one another. An optical filter, e.g., a bandpass filter, dual bandpass filter or triple bandpass filter is optionally arranged in front of the emitter 5. A detector 4 is arranged at the plane mirror 6 spaced apart from the light source (radiation source) 2 and oriented in the direction of the concave mirror 7. The detector 4 is configured for measuring the intensity of the light waves. The concave mirror 7 comprises an optical axis 8, which is arranged essentially at right angles to the plane mirror 6. The distance of the concave mirror 7 to the emitter 5 is approximately half of the radius of curvature of the concave mirror 7 in this first embodiment. When using an optical filter arranged in front of the emitter 5, the distance is somewhat greater than half the radius of curvature of the concave mirror 7. Two different light beams L emitted by the radiation source 2 are shown in this view, wherein a first light beam L is schematically shown by a solid line and a second light beam L is schematically shown by a dotted line. The emitted light beams L are each reflected by the concave mirror 7 to the plane mirror 6 and again to the concave mirror 7 until they reach the detector 4. This arrangement is especially advantageous when the gas G to be measured absorbs light waves L only weakly and when the gas sensor 1 has to have an as compact as possible size.

Figure 2:
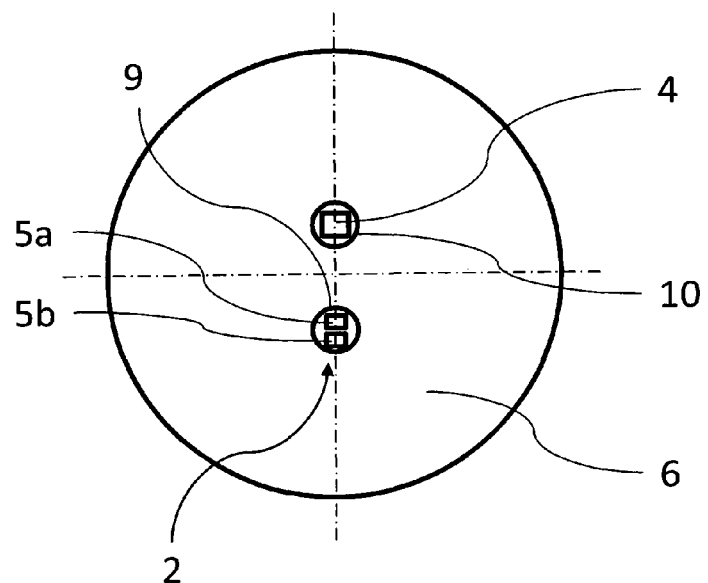
FIG. 2 is a schematic top view of a plane mirror of the gas sensor according to the present invention from FIG. 1.

FIG. 2 shows the plane mirror 6 of the first embodiment of the gas sensor 1 in a top view. The plane mirror 6 comprises a first aperture 9, in which a radiation source 2 with a first emitter 5a as well as with a second emitter 5b is arranged, and a second aperture 10, in which the detector 4 is arranged. This first embodiment of the gas sensor 1 according to the present invention is especially suitable for quantitatively measuring the concentration of a gas or for detecting an individual gas G. For this, light waves L of different wavelengths can be alternately emitted and/or be modulated with different frequencies by the first emitter 5a and by the second emitter 5b. The detector 4 determines the intensity of these partially absorbed light waves L. In this case, the light waves emitted by the second emitter 5b can be used as a reference signal. The first emitter 5a and the second emitter 5b are configured as LEDs in this embodiment.

Figure 3:
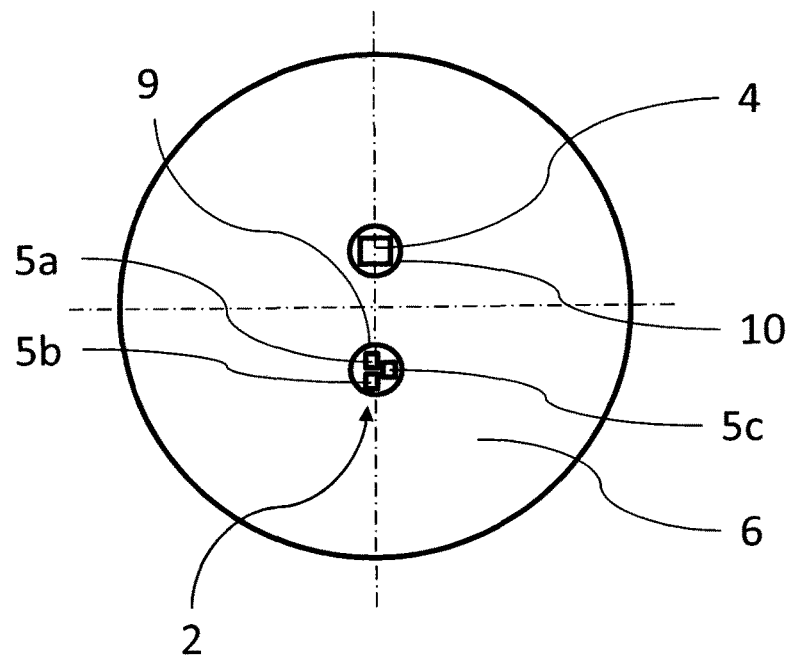
FIG. 3 is a schematic top view of a plane mirror of a second embodiment of a gas sensor according to the present invention.

FIG. 3 shows a plane mirror 6 of a second embodiment of the gas sensor according to the present invention in a top view. The plane mirror 6 comprises a first aperture 9, in which a radiation source 2 with a first emitter 5a, with a second emitter 5b as well as with a third emitter 5c is arranged, and a second aperture 10, in which the detector 4 is arranged. An optical filter, e.g., a bandpass filter, dual bandpass filter or triple bandpass filter is optionally arranged in front of the first emitter 5a and/or the second emitter 5b and/or the third emitter 5c. The first emitter 5a, the second emitter 5b and the third emitter 5c are configured as LEDs in this embodiment. The second embodiment of the gas sensor 1 differs from the first embodiment by the radiation source additionally comprising a third emitter 5c. This second embodiment of the gas sensor 1 according to the present invention is especially suitable for quantitatively measuring or for detecting two different gases G. For this, light waves L of different wavelengths can be emitted by the first emitter 5a, the second emitter 5b and the third emitter 5c. The detector 4 determines the intensity of these partially absorbed light waves L. In this case, e.g., the light waves emitted by the third emitter 5c are used as a reference signal.

Figure 4:
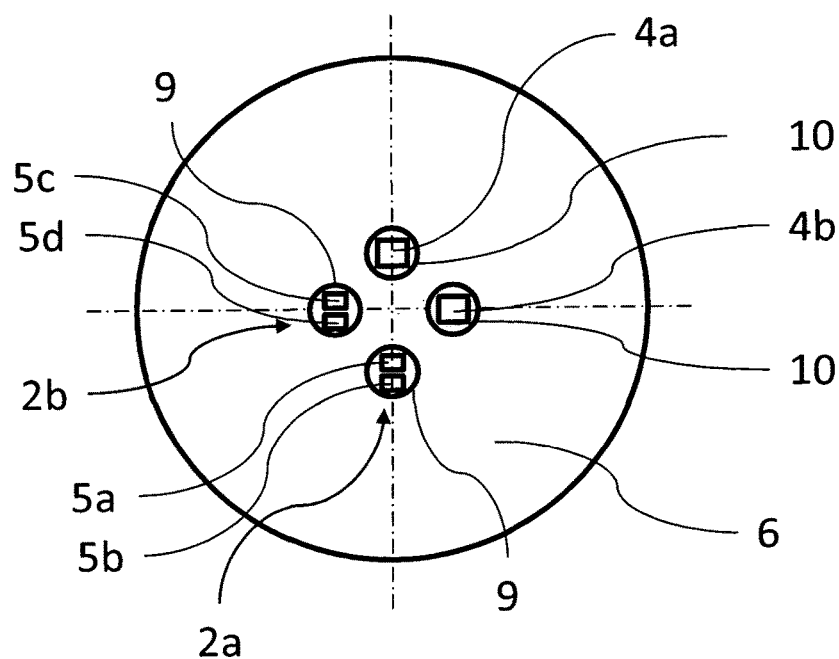
FIG. 4 is a schematic top view of a plane mirror of a third embodiment of a gas sensor according to the present invention.

FIG. 4 shows a plane mirror 6 of a third embodiment of the gas sensor 1 according to the present invention in a top view. The plane mirror 6 comprises two first apertures 9 and two second apertures 10. A first radiation source 2a with a first emitter 5a as well as with a second emitter 5b is arranged in a first aperture 9. A second radiation source 2b with a third emitter 5c as well as with a fourth emitter 5d is arranged in the other first aperture 9. A first detector 4a is arranged in a second aperture 10 and a second detector 4b is arranged in the other second aperture 10. The third embodiment of the gas sensor 1 differs from the first embodiment by the gas sensor 1 comprising two radiation sources 2 as well as two detectors 4. Light waves emitted by the first radiation source 2a can be detected preferably exclusively or essentially by the first detector 4a and light waves emitted by the second radiation source 2b can be detected exclusively or essentially by the second detector 4b. During operation the first radiation source 2a and the second radiation source 2b can simultaneously emit light waves L. The first emitter 5a, the second emitter 5b, the third emitter 5c and the fourth emitter 5d are configured as LEDs in this embodiment. This third embodiment of the gas sensor 1 according to the present invention is especially suitable for simultaneously quantitatively measuring and detecting two different gases G in a gas mixture. Bandpass filters, which are arranged in front of the radiation sources 2 or detectors 4, act as mirrors for light waves of each of the other radiation sources 2. This increases the efficiency of the gas sensor 1.

While specific embodiments of the invention have been shown and described in detail to illustrate the application of the principles of the invention, it will be understood that the invention may be embodied otherwise without departing from such principles.

The invention claimed is:

1. An optical gas sensor for quantitatively measuring the concentration of one or more gases, the optical gas sensor comprising:

a radiation source for emitting light waves;

a cuvette for holding a gas to be measured; and a detector for measuring light intensities, wherein:

the radiation source comprises a first emitter and a second emitter, the first emitter being configured to emit light waves of a first wavelength and the second emitter is configured to emit light waves of a second wavelength, the second wavelength being different from the first wavelength, and the detector comprising at least one optical filter, the radiation source being configured to emit the light waves of the at least one first wavelength and of the second wavelength simultaneously as well as separately from one another;

the cuvette comprising a mirror arrangement with a plane mirror and a concave mirror arranged opposite the plane mirror, wherein an optical axis of the concave mirror is arranged essentially at right angles to the plane mirror, wherein the plane mirror has a first aperture and a second aperture, wherein the first aperture has at least two emitters;

the emitter is configured to emit a spectrum, the full width at half maximum of which is a maximum 50% of the effective wavelength; and the detector being configured to receive the first and second wavelengths and to separately quantitatively detect an intensity of the emitted light waves of the first wavelength and of the second wavelength.

2. An optical gas sensor in accordance with claim 1, wherein the radiation source is configured to emit a discrete spectrum of light waves, the full width at half maximum of which is a maximum 20% of the effective wavelength.

3. An optical gas sensor in accordance with claim 1, wherein the radiation source and/or the detector are arranged at the plane mirror.

4. An optical gas sensor in accordance with claim 3, wherein the radiation source and the detector are arranged at the cuvette such that light waves emitted by the radiation source reach the detector directly.

5. An optical gas sensor in accordance with claim 1, wherein the radiation source and the detector are arranged at the cuvette such that light waves emitted by the radiation source reach the detector directly.

6. An optical gas sensor in accordance with claim 1, wherein the radiation source is arranged at the cuvette spaced apart from the detector, the emitter being configured to emit light waves with a controlled beam path.

7. An optical gas sensor in accordance with claim 1, wherein the detector is precisely one detector that is arranged at the cuvette.

8. An optical gas sensor in accordance with claim 1, wherein at least two radiation sources are arranged at the cuvette spaced apart from one another.

9. An optical gas sensor in accordance with claim 8, further comprising another detector to provide two detectors, wherein the cuvette comprises at least the two detectors, the two detectors being configured to measure light intensities of different radiation sources or of different emitters of the two radiation sources.

10. An optical gas sensor in accordance with claim 1, wherein:
   said detector receives both the first and second wavelengths at a single location.

* * * * *